United States Patent [19]

Grande

[11] Patent Number: 4,846,835
[45] Date of Patent: Jul. 11, 1989

[54] TECHNIQUE FOR HEALING LESIONS IN CARTILAGE

[76] Inventor: Daniel A. Grande, 12 Laurel Ave., Glen Cove, N.Y. 11542

[21] Appl. No.: 61,952

[22] Filed: Jun. 15, 1987

[51] Int. Cl.$^4$ .............................................. A61F 2/02
[52] U.S. Cl. ...................................... 623/11; 623/13; 623/16
[58] Field of Search ................. 128/92 W; 623/1, 11, 623/16, 13

[56] References Cited

U.S. PATENT DOCUMENTS

| | | | |
|---|---|---|---|
| 3,949,073 | 4/1976 | Daniels et al. | 424/177 |
| 3,992,725 | 11/1976 | Homsy | 623/16 X |
| 4,356,261 | 10/1982 | Kuettner | 424/95 X |
| 4,439,152 | 3/1984 | Small | 128/92 R X |
| 4,485,097 | 11/1984 | Bell | 424/95 |
| 4,546,500 | 10/1985 | Bell | 623/1 |
| 4,553,272 | 11/1985 | Mears | 623/1 |
| 4,642,120 | 2/1987 | Nevo et al. | 623/11 X |
| 4,681,763 | 7/1987 | Nathanson et al. | 424/95 |

*Primary Examiner*—Tony M. Argenbright
*Attorney, Agent, or Firm*—Michael Ebert

[57] ABSTRACT

A grafting technique entailing the transplantation of chondrocytes for promoting the healing of lesions in articular cartilage, use being made for this purpose of in vitro autologous cultured chondrocytes prior to transplantation. The chondrocytes are preferably seeded in a three-dimensional collagen matrix which serves as the graft material. In order to internally fix the graft during the healing process, use is made of a periosteal flap which is sutured to the cartilage after the graft material is implanted therein.

4 Claims, No Drawings

TECHNIQUE FOR HEALING LESIONS IN CARTILAGE

BACKGROUND OF INVENTION

1. Field of Invention

This invention relates generally to techniques for healing lesions in cartilage, and more particularly to a technique in which lesions in articular cartilage are healed by using in vitro cultured chondrocytes as autografts.

2. Status of Prior Art

The concern of the present invention is with cartilage, an important constituent of which is collagen. Hence by way of introduction, we shall first briefly consider the nature of collagen, a substance which accounts for about thirty percent of the total human body protein. Collagen, which has a characteristic amino acid composition, forms the fibrillar component of soft connective tissues such as skin, ligament and tendon, and is the major component of the organic matrix of calcified hard tissues such as bone and dentine. Quite apart from its structural significance, collagen plays an important role in development and in wound healing.

There exist at least four genetically distinct types of collagen. The most familiar, type I, consists of three polypeptide chains. Two chains are identical and are called $\alpha 1(I)$; the third being called $\alpha 2$. Type I collagen forms the major portion of the collagen of both soft (skin, tendon and hard (bone and dentine) connective tissue. Type II collagen is the major collagen of cartilage and is composed of three $\alpha 1(II)$ chains. Type III collagen is composed of three $\alpha 1(III)$ chains and is found in blood vessels, wounds, and certain tumors. Reticulin fibers appear to be identified with type III collagen. Basement membrane collagens are classified as type IV.

The intercellular substances of connective tissue are classified as either amorphous or fibrous. The former exist as firm or soft gels. These are mucopolysaccharides containing bound water which permits diffusion to take place through them. Fibrous intercellular substances are commonly immersed in the amorphous type and assume various forms, such as the white fibers of collagen, yellow fibers constituting an elastin, and reticular fibers in the form of lacy networks that give intimate internal support to cells. Connective tissue cells that generate intercellular substances thereafter lie within the substances they have formed.

Cartilage, which is a specialized kind of connective tissue, serves as the model for most bones during development, and it persists in adults in certain limited regions in three forms: hyaline or glassy cartilage; elastic cartilage and fibrocartilage.

Hyaline cartilage is found in joints, at the ventral ends of ribs and in other regions of the body. The cartilage cells or chondrocytes take up about one third of the volume of the cartilage, the rest being occupied by the matrix which separates the cells and contains collagen fibers. Since cartilage has no blood vessels, exchanges with blood occur over longer distances than in other forms of connective tissue.

Elastic cartilage, which is found in the external ear, in the epiglottis and at other sites, is more opaque and flexible than hyaline cartilage and is rich in elastic fibers. Fibrocartilage, which occurs in certain tendons near their attachment to bones, is constituted by dense bundles of collagen fibers, the cells being disposed in columns between these fibers.

The intercellular substance of cartilage is chiefly composed of a mucopolysaccharide gel and collagen fibers. The cells which create this intercellular substance are called chondroblasts, and after making this substance they lie within it as chondrocytes.

Appended to this specification is a listing of cited prior art publications which identify the authors, the published papers and their publishers, and also give the relevant page numbers. In the discussion to follow, these papers will be referred to only by their authors and year of publication.

Articular cartilage is classified as a connective tissue along with bone and ligaments (Bloom and Fawcett, 1975). Articular cartilage combines two components; namely, a cellular component comprising the chondrocytes, and an extracellular matrix which consists of collagen and proteoglycan. Articular cartilage is found at the articulating ends of most diarthodial synovial joints (Gray, 1973).

It has long been believed that once articular cartilage is damaged it is incapable of repair (Hunter, 1743; Paget, 1853). This characteristic is attributed to the lack of blood and nervous supply to this type of connective tissue (Barnett, 1961; Brower and Akahosi, 1962; McKibbin, 1973). In vascularized tissues, there are three well-documented phases of response to injury which are lacking in articular cartilage following injury (Paget, 1853; Mankin, 1982). Due to the vascular supply of the subchondral bone, lesions which fracture it undergo the three normal stages of repair: necrosis, inflammation, and healing. The repair tissue in these defects, however, is fibrocartilage containing type I collagen which does not have the same biomechanical/biochemical character as hyaline cartilage which is comprised of predominantly type II collagen (Campbell, 1969).

Cartilage defects which do not fracture the subchondral plate can progress to necrosis but not inflammation or repair. Studies of these defects have indicated that initially there is a heightened metabolic activity demonstrated by an increased uptake by chondrocytes of sulphate and glycine (Mankin and Lipiello, 1969; Mankin, 1982). However, these attempts at repair are short-lived and after one week the increased synthesis of matrix products usually returns to normal levels of activity. Long term observation shows that these lesions do not heal significantly (Mankin,1982).

The question of whether articular cartilage has an intrinsic ability to heal after injury has not been adequately answered (Hunter, 1743; Redfern, 1851; Paget, 1853; Mankin, 1982; Sokoloff, 1984). In reviewing the literature, it becomes apparent that the results reported by various investigators have been far from unequivocal. Two possible mechanisms may exist by which repair may be initiated (Sokoloff, 1974, 1978). First is replication of chondrocytes in the regions adjacent to a defect, also termed "intrinsic" repair. Second, is metaplasia of cartilage from other para-articular connective tissue within the joint capsule such as synovium and subchondral bone, termed "extrinsic" repair. To what degree either of these mechanisms can contribute to the total restoration of a joint surface is unknown.

It is possible to characterize three basic types of defects in articular cartilage after injury. A type I defect consists of scarification of the articular surface, similar to the fibrillar changes that can be seen in early degenerative joint disease (Meachim, 1963; Mankin, 1982). A type II defect is comparable to the erosive thinning that occurs in rheumatoid arthritis and in osteoarthritis (DePalma et al., 1963, 1966; Green, 1977, Mankin, 1982). A type II defect penetrates all layers of cartilage down to but not including the subchondral plate. A type III defect is a full-thickness cartilage defect with some loss of subchondral bone. Type III defects can be compared to osteochondral fractures or drill defects.

There is confusion in the literature over the definition of "full-thickness cartilage defects" both clinically and experimentally. Some authors define full-thickness defects as being those that include fracturing of the subchondral plate; others define it as penetration of all layers of cartilage without violation of the subchondral bony plate (Kennedy et al., 1967; Salter, 1980; Rubak et al., 1982A, 1982B; Johnson-Nurse and Dandy, 1985). Injuries producing types I and II defects exhibit a similar minimum degree of repair. Due to the vascular supply of the subchondral bone, type III lesions undergo the three normal stages of repair: necrosis, inflammation, and healing.

The idea of allografting to heal lesions in articular cartilage goes back over a century (Hunter, 1943; Bert, 1865; Zhan, 1877; Tizzoni, 1878; Dupertius, 1941). Early investigators also observed that any cartilaginous tissue produced following an injury was not hyaline cartilage but fibrocartilage (Redfern, 1851; Paget, 1953).

Two separate techniques are currently used in cartilage transplantation research: (1) the transplantation of osteochondral grafts, and (2) the transplantation of chondrocytes. Numerous attempts have been made to transplant whole or partial joints with mixed results (DePalma et al., 1963; Seligman, 1972). The availability of clostridial collagenase to enzymatically isolate chondrocytes from their matrix made it possible to attempt culture as well as transplantation of chondrocytes (Smith, 1965; Manning and Bonner, 1967). Subsequently, many investigators have attempted to successfully heal cartilage defects using the method of chondrocyte transplantation. Earlier studies reported using chondrocytes isolated from epiphyseal plates (Chesterman and Smith, 1968; Bentley and Greer, 1971; Green, 1977; Bentley et al., 1978) as well as articular chondrocytes (Chesterman and Smith, 1968; Green, 1977).

It was believed that the epiphyseal cells would perform better as grafts due to their heightened metabolism. However, these grafts generally did not heal well, probably due to their fate of eventual hypertrophy, necrosis, and calcification (Bloom and Fawcett, 1975). Techniques using drills to create defects (Bentley and Greer, 1971; Bentley et al., 1978) may suffer from two shortcomings: (1) Defects are not reproducibly made to the same depth. Violation of the subchondral plate may therefore have occurred. (2) Heat dissipated by drill friction may cause local necrosis in the adjacent matrix.

In the numerous reports of chondrocyte transplantation since the introduction of collagenase, none has addressed a method for internal surgical fixation of the grafted cells in vivo. This could possibly account for the reported low incidence of healing. It would seem improbable that a graft of free cells would remain within a defect in the joint environment without diffusing outward. Another problem remains in that freshly isolated cells, being relatively small in number and having recently been traumatized by the rigors of enzyme digestion, would have a minimum potential to reconstitute defects. In addition, some authors provide results distinguishing between autograft and allograft transplants (DePalma et al., 1966), while others do not (Chesterman and Smith, 1968; Green, 1971, 1977; Green and Ferguson, 1975).

Injury to articular cartilage is probably more frequent than is diagnosed either by clinical or radiographic examination. It has been noted that localized articular cartilage lesions were found in 30 to 60% of acute and chronic knee injuries in humans (Clancy et al., 1983) and occur in a variety of injuries such as blunt trauma, fractures, and dislocations. At present, the available treatment for these lesions, which includes excision and drilling, articular cartilage debridement, arthroscopic shaving, and abrasion arthroplasty, shows that optional resurfacing in human patients is not achieved because only fibrocartilaginous repair is the result (Magnuson, 1941; Henche, 1967; Insall, 1967; Mitchell and Shepard, 1978; Johnson, 1981).

SUMMARY OF INVENTION

In view of the foregoing, the main object of this invention is to provide a grafting technique which makes use of chondrocyte transplantation to promote healing of lesions in articular cartilage.

More particularly, an object of this invention is to provide a grafting technique for effecting hyaline cartilage repair which makes use of in vitro autologous cultured chondrocytes prior to grafting.

A salient feature of the invention is that by using autologous chondrocytes for transplantation, it excludes variable immunological reactions. And with the advent of early diagnosis via arthroscopy, the invention provides a technique for hyaline cartilage repair that is useful clinically in the treatment of isolated traumatic cartilage lesions detected by such diagnoses.

Still another object of the invention is to provide for use in the above-noted grafting technique an activated matrix formed by a collagen body having dispersed therein the chondrocytes to be transplanted, the collagen serving to enhance the healing process.

Also an object of the invention is to provide a grafting technique of the above type which effects mechanical fixation of the graft to facilitate regeneration of the injured cartilage.

Briefly stated, these objects are attained in a grafting technique entailing the transplantation of chondrocytes for promoting the healing of lesions in articular cartilage, use being made for this purpose of in vitro autologous cultured chondrocytes prior to transplantation. The chondrocytes are preferably seeded in a three-dimensional collagen matrix which serves as the graft material. In order to internally fix the graft during the healing process, use is made of a periosteal flap which is sutured to the cartilage after the graft material is implanted therein.

DESCRIPTION OF INVENTION

Basic Concept:

It has been found that the healing of articular cartilage lesions which do not fracture the subchondral plate can be enhanced by using in vitro cultured chondrocytes as autografts. These chondrocytes are grown in culture (for two to three weeks) and then auto-transplanted back into the defect. In practice, this procedure has resulted in 80% reconstitution of defects at about six weeks following initial grafting. In addition, knee joints which receive such grafts characteristically exhibit amelioration of degenerative changes.

In a preferred technique, the chondrocytes are grown in a three-dimensional collagen matrix to provide the desired graft material. In practice, the chondrocytes are isolated enzymatically and seeded in a collagen gel. The use of a collagen gel to keep the chondrocytes fixed in situ appears to have distinct advantages over the use of free cells.

In order to internally fix the graft, a periosteal flap is used for this purpose. Periosteum appears to possess an intrinsic capability of providing regeneration of cartilage.

Studies:

In investigating a technique in accordance with the invention for enhancing the healing of defects in articular cartilage using chondrocyte transplantation, the following studies were made:

The knee joints of adult New Zealand White (NZW) rabbits were used for the model in this investigation. An initial baseline study (n=5) was made to determine what intrinsic capability cartilage has for healing defects which do not fracture the subchondral plate. Surgical arthrotomy was performed on the right knee joint with the left knee of the same animal serving as a sham control in which the joint capsule was opened surgically and then closed with sutures. The right patella was everted laterally and a 3 mm diameter full-thickness mid-patella defect (Type II) was made using a sharpened stainless steel trefine punch. The cartilage within the defect was removed and curetted down to, but not through, the subchondral plate. The status of these defects at six weeks postoperatively showed that there was little repair. Macroscopic and histological finding were consistent with the onset of osteoarthritis such as synovitis and "cell nests." The mean amount of tissue which was reconstituted was 16.5% was measured by quantitative 2-D image analysis.

A second experiment examined what effect autologous in vitro grown chondrocytes had on the healing of these defects. In this experiment (n=10), defects were created surgically in both patellae. The cartilage removed was collected aseptically in saline. Free chondrocytes were isolated from the cartilage samples using a proteolytic enzyme digestion and grown in vitro for 2-3 weeks. At this time, the original donor rabbit was again prepared for surgery. The chondrocytes were trypsinized, washed, and spun into a pellet. The chondrocyte pellet was pipetted into the defect previously created in the right patella. The cells were fixed in situ with a 3 mm diameter piece of periosteum with the cambium layer facing downward (into the defect) and held by four 9-0 vicryl interrupted sutures. The left patella served as the control side and received a periosteal flap but not the autologous chondrocyte graft. Animals were sacrificed six weeks post-operatively. Macroscopic results from grafted specimens displayed a significant decrease in synovitis and other degenerative changes as assessed by chi-square analysis. Defects which had received transplants also had a significant amount of cartilage reconstituted (82%) compared to ungrafted controls (18%). Controls showed healing comparable to that obtained in the initial baseline study. The repair cartilage appeared hyaline with viable chondrocytes in lacunae. Complete joint surface restoration was seein in 25% of grafted samples.

The technique of using a periosteal flap to internally fix the graft was conceived after a series of studies (Rubak, 1982a, 1982b; O'Driscoll, 1985, 1986) reported on the chondrogenic potential of free autogenous periosteal grafts. Our work showed that periosteum alone had very little intrinsic chondrogenic potential. In the previous studies, the defects made included fracture of the subchondral plate (Type III defect). These defects will heal with fibrocartilage either in the presence or absence of periosteum and/or continuous passive motion. (O'Driscoll, 1986). These defects will heal with fibrocartilage either in the presence or absence of periosteum and/or continuous passive motion. O'Driscoll (1986), in an extensive study, reported that 70% of this reconstituted cartilage was hyaline. While this is a substantial amount of type II collagen, anything but 100% type II should be considered sub-optimal for long term healing.

To determine the source of the chondrocytes in the repair tissue, a third experiment involved grafts with chondrocytes which had been labelled with a radiotracer ($H^3$ thimidine) prior to autologous grafting. A series of rabbits (n=4) received grafts similar to those described in the second experiment. Six weeks post-operatively, animals were sacrificed and cartilage samples were prepared for autoradiography. The results of this experiment showed that a small percentage of the cells in the reconstituted matrices were labeled (approximately 10%). From these results it can be inferred that grafted chondrocytes were actively dividing and therefore a reduction or dilution of label was seen. These results indicate that chondrocyte transplantation is a viable method of treating certain lesions in articular cartilage. They show that isolated defects who go untreated in articular cartilage do progress toward a degenerative joint disease similar to osteoarthritis. The lower incidence of synovitis observed in grafted specimens is of significant clinical value.

MATERIALS AND METHODS

Surgical Procedure I:

This procedure is used to create full-thickness cartilage defects and for collection of cartilage samples for subsequent chondrocyte isolation and culture. The animal models were skeletally mature male New Zealand White (NZW) rabbits.

All surgical procedures are performed using general anesthesia initiated with an injection of Ketamine (100 mg/ml) at 350 mg/kh body weight and Xylazine (20 mg/ml at 5 mg/kg body weight (supplied by Northern Veterinarian Supply Company) administered intramuscularly in the hind extremity. After being placed under general anesthesia, the NZW rabbits are shaved of all hair in the knee region of both knees. The rabbits are placed in a supine position on an operating table. Both knees are painted three times with Betadine, then draped with sterile towels to create a sterile surgical field. The patella is located by palpating the knee region and a medial longitudinal parapatellar skin incision is made. Subcutaneous connective tissues, muscle, and joint capsule are incised in line with the initial skin incision. Hemostasis is maintained by the use of an electric cautery which is used sparingly and only on profusely bleeding vessels to avoid large foci of necrotic tissue. The patella is everted laterally to expose the articular surface and care is taken to avoid abrasion of the articular surface as well as trauma to the adjacent tissues. A 3 mm diameter full-thickness mid-patella defect is made using a sharpened stainless steel punch.

The articular cartilage within the created defect is removed with a number 15 scalpel and the defect is curetted down to, but not through, the subchondral bony plate. The articular cartilage obtained is immediately placed in sterile tubes of phosphate buffered saline. If the sample is to receive a homologous allograft, surgical procedure (2) would be implemented here. An autologous graft would require a separate surgical procedure at a time point 2–3 weeks later; therefore, surgical procedure (1) is continued. The patella is reduced to its anatomical position and the field is irrigated with normal saline. The wound is closed in layers, using 5-0 vicryl interrupted sutures. After closing the joint capsule, the joint is inspected to insure sufficient strength in the sutures in order to keep the patella from dislocating during normal use. The skin is closed and the rabbit returned to its cage where it is allowed unlimited movement and food and water ad libidum.

Chondrocyte Isolation and Primary Culture

All in vitro manipulations are performed in a laminar flow hood using aseptic technique. The cartilage samples obtained from each rabbit are treated as follows to isolate free chondrocytes. The cartilage specimens are transferred to sterile 60 mm petri dishes and diced into pieces approximately one cubic millimeter and then transferred to a glass spinner flask. To this flask is added 15 ml of RPMI-1640 Medium with 25 mm HEPES buffer (MA Bioproducts) containing clostridial collagenase (Type 1A 0.37 mg/ml), deoxyribonuclease (DNAse) (activity - 133 U/mg, 15 mg/ml), testicular hyaluronidase (Type 1S; 1 mg), and penicillin/streptomycin (5000 U/5000 U; 1% V/V). All enzymes purchased from Sigma Chemical Company, St. Louis, Mo. This enzyme/medium mixture is filter sterilized (0.2 $\mu$M, Nylon membrane) and added in a manner to wash the cartilage pieces down the sides of the flask to the bottom. The samples are spun on a magnetic stirrer at 37° C. for 12-18 hours at a slow speed of approximately 30–40 RPM.

In order to harvest the cells, extracellular matrix debris is removed by passing the entire medium/cell mixture through a sterile nylon mesh (Nytex Corporation, 120 $\mu$M). This is followed by centrifuging at 1500 RPM for 5 minutes. The cell pellet is resuspended with phosphate buffered saline and centrifuged. The washing procedure is repeated twice. The total number of cells is estimated by counting using a standard Neubauer hemocytometer. Viability of the isolated cells is tested by the Trypan blue exclusion method (Freshney, 1983).

Chondrocytes are seeded into 24 $cm^2$ polystyrene flasks (Falcon Plastics) in an incubator with an environment of 5% $CO_2$, 95% humidity, and a temperature of 37° (Hot Pack Corporation, Model 351920). The growth medium consists of RPMI-1640 which is supplemented with 10% fetal bovine serum, L-glutamine (2 mM) and a mixture of penicillin/streptomycin (5000 U/5000 U, 10 cc/500 ml). Cultures are fed fresh medium every other day, and examined daily for growth using an inverted phase contrast light microscope (Leitz diavert).

When the cells become confluent, they are passed by trypsinization (trypsin, 0.25% V/V in HBSS without Ca++ and Mg++). The medium in which the cells are growing is aspirated and replaced with 2 cc of the trypsin medium followed by incubation at 37° for 15 minutes. The flask is then examined with a microscope to make certain that the cells are becoming detached from their substrate. The medium and cells are then centrifuged and washed three times with PBS. The cells are counted and passed to a three-dimensional collagen matrix (Vitrogen TM collagen gel, collagen sponge, or antigen-extracted cartilage tissue). They are grown in a collagen matrix for two weeks, and then prepared for either autologous or homologous transplantation.

Surgical and Transplantation Procedure II

The following transplantation procedure is performed on only the right knee joint of the rabbits which has already bilaterally undergone the initial surgical procedure (1) described earlier and from which chondrocytes have been harvested. The right patella serves as the experimental side, receiving the chondrocyte transplant into the previously-made defect. The left patella serves as the control in which the defect is created by surgical procedure (1), but no chondrocyte graft is subsequently transplanted.

Three weeks after the initial surgical procedure (1), when articular cartilage was removed for culture, the rabbits are again placed under general anesthesia, shaved and draped as described previously. In the right knee, a skin incision is made in line with the previous medial parapatellar incision. The knee joint is opened as previously described and examined for the presence of synovitis and/or degenerative change. The status of the patellar defects is noted.

Various materials were evaluated in regard to their ability to anchor a graft in situ, and it was found that periosteum is most effective for this purpose. The procedure for using periosteum is as follows: The periosteum on the medial aspect of the proximal tibia is exposed and isolated. With a scalpel, a circular area of periosteum 3 mm in diameter was removed. This periosteum is sutured to the periphery of the patella defect with the cambium layer facing down using four interrupted 9-0 vicryl sutures. The last suture is left untied to permit introduction of the cultured chondrocyte graft. The chondrocyte graft is placed into the defect. The fourth suture is tied to secure the periosteum covering over the defect. The patella is reduced and the wound closed in layers. The identical procedure is performed on the left knee, except that no chondrocyte graft is transplanted into the defect.

Standard Tissue Processing:

Rabbits are sacrificed in groups at different time periods post-operatively by an injection of T-61 euthanasia solution (0.2 ml/kg body weight). At sacrifice, the knee joints are examined. Any indication of synovitis and/or degenerative changes are subjectively graded as absent, mild, moderate, and severe. The other parameters graded will be color of the cartilage, presence of intra-articular adhesions, and the contour and smoothness of the articular surface of the patella. Patella samples are kept moist in saline and then photographed.

Both control and experimental specimens are fixed in neutral buffered formalin for 24 hours. Prior to further processing, the area of the defect is marked with a drop of India ink to later facilitate precise bisecting of the patella. India ink is used because it does not wash out of the tissue during decalcification. The specimens are decalcified with 0.1 m EDTA (pH 7.0) until roentgenographs taken at 24 intervals show no undecalcified areas. The usual decalcification time is 48 hours. The patellae are then bisected sagitally through the center of the defect, dehydrated, and embedded in paraffin. Sections are cut sagittally at 5 $\mu$m in thickness and stained with hematoxylin and eosin, Safranin-0, and Sirius red F3BA (Junquiera et al., 1982).

Histological Measurements:

Quantitative stereology were performed using a Zeiss Videoplan analyzer. Slides are scanned under low power at x40 to ascertain the boundaries of the original defect. If the borders of the defect are not self-evident, the side which demonstrates the clearest edge is used as a reference point, and a reticle eyepiece is used to measure a distance of 3 mm. The area measured for percent reconstituted is derived by the formula: area reconstituted/area of the original defect $\times$ 100. Four boundary surfaces are defined for the area of the original defect. The first and second surfaces comprise the lateral aspects of an original defect from the articular surface superiorly to the cartilage-bone interface inferiorly. The third superior boundary is defined as a line drawn along the articular surface bridging any regions which had not completely healed. The fourth surface connects the inferior ends of the two lateral boundaries along the surface formed by the cartilage-bone interface. These four surfaces complete a rectangle which is defined as area of original defect. Using the Zeiss Videoplan digitizer, tracings are then made of the area of tissue which has subsequently filled in. This is defined as the area reconstituted. The Zeiss Videoplan gives an absolute measurement of area.

The Activated Matrix:

A preferred procedure for producing the graft material is to first grow the cells to be transplanted in a monolayer culture on a flat substrate for about one week in order to greatly increase their number. Then the cells are removed by an enzyme from the flat substrate and uniformly dispersed within a suspension of collagen gel which has not yet polymerized. Once the gel sets, the cells are suspended at fixed sites throughout the matrix which is now in an activated state.

It is important to note the advantages gained by the use of a collagen matrix. Collagen, which is present in all animals, is not antigenic and is therefore not rejected. Also, collagen promotes the healing of wounds and thereby facilitates the healing activitity of the chondrocytes. In lieu of using a gel-type collagen as the matrix, use may be made of collagen in reticulated or sponge-like form having the chondrocytes embedded therein. A preferred matrix can be created by injecting a suspension of collagen gel which has not yet polymerized and which has cells uniformly dispersed therein into the pores of a collagen sponge to produce a composite having superior material properties and handling characteristics than the above matrices.

Conclusions:

The results of our studies and experiments indicate that in the rabbit, knee chondrocyte autografts significantly improve the reparative capability of articular cartilage as measured by quantitative histological analysis. Macroscopic observation showed that the knee joint treated had a lower incidence of synovitis than controls. Although the use of the chondrocyte grafting technique did not result in a 100% healing rate, in all experimental specimens the defect areas were filled with cartilage, whereas control specimens had well demarcated defects which were visually not healed.

Results obtained from transplants with cells labeled with tritiated thymidine showed that chondrocytes which occupy reconstituted defect areas have only a small percentage of labeled cells, approximately eight percent. Once labeled cells are transplanted, if they were to further undergo division in vivo, labeling intensity would decrease with time. In our studies, 100% of the transplanted cells were labelled at the time they were grafted. Six weeks later, eight percent of the cells remained labeled. Therefore, the transplanted cells had become incorporated into the reconstituted cartilage matrix. These findings support our hypothesis that the chondrocytes have indeed survived and proliferated, rather than acting as an inducing agent which has allowed surrounding cells to regenerate cartilage matrix into the defects in an intrinsic type of repair.

The unique feature of the present invention does not lie in the use of chondrocytes as grafts for the purpose of healing articular cartilage lesions, for this is not new. It resides in the use of in vitro autologous cultured chondrocytes prior to grafting, for this has distinct advantages that are lacking in prior chondrocyte grafts. Thus with an ordinary transplant there is always the possibility that the transplant will become immunologically compromised, whereas with the present technique which uses autologous chondrocytes for transplantation, the variable of immunological reaction is excluded thereby.

In prior chondrocyte grafting techniques, no means were provided to effect mechanical fixation of the graft into the defect, and there was therefore no assurance that the graft would remain in place during the prolonged healing process. In the present technique, a sutured periosteal flap was found to afford the desired degree of fixation, whereas other means for this purpose such as fascia, synovium and clotted blood have proven to be unsatisfactory. The advantage of periosteal as the flap material is that it possesses the inherent capability of providing regeneration of cartilage.

While there has been disclosed a grafting technique and preferred grafting materials therefor to promote the healing of cartilage lesions which in the absence of this technique would result in degenerative changes in the cartilage, it is to be understood that various changes and modifications may be made therein based on the teachings of the invention.

The technique described above is applicable as a bridging material for proper healing of epiphyseal plate fractures. The technique is also applicable to the healing of lesions in nasal septums, trachea, ribs and in other regions that call for hyaline cartilage as the healing agent. And in lieu of a periosteal flap, one may use a resorbable biocompatible polymer for the same fixation purpose; such polymers being presently used as suture materials.

PRIOR PUBLICATIONS

1. Barnett, C., Davies, D., and MacConaill, M., 1961: Synovial Joints, Their Structure and Mechanics. C. Thurgood, Ed., Springfield, Ill.
2. Bentley, G. and Greer, R., 1971: Homotransplantation of Isolated Epiphyseal and Articular Cartilage Chondrocytes into Joint Surfaces of Rabbits. Nature, 230:385–388.
3. Bentley, G., Smith A. V., and Mukerjhee, R., 1978: Isolated Epiphyseal Chondrocyte Allografts into Joint Surfaces. An Experimental Study in Rabbits. Ann. Rheum. Dis., 37:449–458.
4. Bert, P., 1865: Sur la Greffe Animale. Compt. Rend. Acad.d. Sc., 61:587. (Cited by Dupertius, 1941.)
5. Bloom, W. and Fawcett, D., 1975: A Textbook of Histology. 10th Ed., W.B. Saunders Co., Philadelphia, Pa.

6. Brower, T. D. and Akahosi, Y., 1962: The Diffusion of Dyes Through Articular Cartilage In Vivo. J. Bone Joint Surg., 44A:456–463.
7. Campbell, C. J., 1969: The Healing of Cartilage Defects. Clin. Orthop. Rel. Res., 64:45–63.
8. Chesterman, P. J. and Smith, A. V., 1968: Homotransplantation of Articular Cartilage and Isolated Chondrocytes—An Experimental Model in Rabbits. J. Bone Joint Surg., 50B:184–197.
9. Clancy, W. G., Shelbourne, K. D., Zoellner, G. B., Keene, J. S., Reider, B., and Rosenberg, T., 1983: Treatment of Knee Joint Instability Secondary to Rupture of the Posterior cruciate Ligament. J. Bone Joint Surg., 65A:310–322.
10. DePalma, A., Tsa-Hos, T., and Maaler, G., 1963: Viability of Osteochondral Grafts as Determined by Uptake of S-35. J. Bone Joint Surg., 45A:1565–1578.
11. DePalma, A. F., McKeever, C. D., and Subin, D. K., 1966: Process of Repair of Articular Cartilage Demonstrated by Histology and Autoradiography with Tritiated Thymidine. Clin. Orthop. Rel. Res., 48:229–242.
12. Dupertius, S. M., 1941: Actual Growth of Young Cartilage Transplants in Rabbits. Arch. Surg., 43:32–63.
13. Gray, H., 1973: Arthrology, Ch. 4, pp. 388–398. In: Grays Anatomy, R. Warwick and P. Williams, Eds., 35th British Edition, Saunders, Philadelphia, Pa.
14. Green, W. T., 1971: Behavior of Articular Chondrocytes in Cell Culture. Clin. Orthop. Rel. Res., 75:248–260.
15. Green, 1977: Articular Cartilage Repair: Behavior of Rabbits Chondrocytes During Tissue Culture and Subsequent Grafting. Clin. Orthop. Rel. Res., 124:237–250.
16. Green, W. T. and Ferguson, R., 1975: Histochemical and Electron Microscopic Comparison of Tissue Produced by Rabbit Articular Chondrocytes In Vivo and In Vitro. Arthritis Rheum., 18:273–280.
17. Henche, H. R., 1967: Patellar Shaving (Indications, Technique, Results) in the Knee. pp. 157–164. In: Ligament and Articular Cartilage Injuries. D. Hastings, Ed., Springer Verlag, New York, N.Y.
18. Hunter, W., 1943: On the Structure and Diseases of Articulating Cartilage. Phil. Trans., B9–267.
19. Insall, N.J., 1967: Intra-Articular Surgery for Degenerative Arthritis of the Knee. J. Bone Joint Surg., 48B:211–288.
20. Johnson, L. L., 1981: Ch. 2, pp. 14–21. in: Diagnostic and Surgical Arthroscopy, (2nd Ed.,). C. Mosby, St. Louis, Mo.
21. Johnson-Nurse, C. and Dandy, D. J., 1985: Fracture Separation of Articular Cartilage in the Adult Knee. J. Bone Joint Surg., 67B:42–43.
22. Kennedy, J. C., Grainger, R. W., and McGraw, R. W., 1967: Osteochondral Fractures of the Femoral Condyles. J. Bone Joint Surg., 49B:436–440.
23. Magnuson, B. P., 1941: Joint Debridement: Surgical Treatment of Degenerative Arthritis. Surgical Gynecol., Obst., 73:1.
24. Mankin, H. J., 1982: The Response of Articular Cartilage to Injury—J. Bone Joint Surg. 64A:460–466.
25. Mankin, H. J. and Lipiello, L., 1969: The Turnover of Adult Rabbit Articular Cartilage. J. Bone Joint Surg., 51A:1591–1600.
26. Manning, W. and Bonner, W., 1967: Isolation and Culture of Chondrocytes from Human Adult Articular Cartilage. Arthritis Rheum., 10:235–239.
27. McKibbin, B., 1973: Nutrition, Ch. 8, pp. 277–286 in: Adult Articular Cartilage. L. Sokoloff (Ed.), Grune and Stratton, New York, N.Y.
28. Meachim, G., 1963: The Effect of Scarification on Articular Cartilage in the Rabbit. J. Bone Joint Surg., 45B:150.
29. Mitchell, N. and Shepard, N., 1978: The Resurfacing of Adult Rabbit Articular Cartilage by Multiple Perforations throughout the Subchondral Bone. J. Bone Joint Surg., 58A:230–233
30. O'Driscoll, S. W., F. W. Keeley and R. B. Salter: Regenerated Articular Cartilage Produced by Free Periosteal Grafts: The Effect of CPM on its Long Term Durability. Transactions of the Orthopaedic Research Society. P. 292, 1985.
31. O'Driscoll, S., Keeley, F., and Salterg, R., 1986: The Chondrogenic Potential of Free Autogenous Periosteal Grafts for Biological Resurfacing of Major Full-Thickness Defects in Joint Surfaces Under the Influence of Continuous Passive Motion. J. Bone Joint Surg., 68A(7):1017–1035
32. Paget, J., 1853: Lecture XII: Healing of Injuries in Various Tissues. Lectures on Surgical pathology, 1:262, London.
33. Redfern, P., 1851: On the Healing of Wounds in Articular Cartilage. Month. J. Med., Sci., 13:201.
34. Rubak. J. M., 1982: Reconstruction Articular Cartilage Defects with Free Periosteal Grafts: An Experimental Study. Acta Orthop. Scand., 53:175–180.
35. Rubak. J. M., Poussa, M., Ritsale, V., 1982: Effects of Joint Motion on the Repair of Articular Cartilage with Free Periosteal Grafts. Acta Orthop. Scand., 53:187–191.
36. Salter, R. B., Simmonds, D. F., Malcom, B. W., Rumble, E. J., MacMichael, D., and Clements, N. D., 1980: The Biological Effect of Continuous Passive Motion in the Healing of Full-Thickness Defects in Articular Cartilage. J. Bone Joint Surg., 62A:12-32–1252.
37. Seligman, G., 1972: Transplantation of Whole Knee Joint in the Dog. Clin. Orthop. Rel. Res., 87:332.
38. Smith, A. V., 1965: Survival of Frozen Chondrocytes Isolated from Cartilage of Adult Mammals. Nature, 205:782–784.
39. Sokoloff, L., 1974: Cell Biology and the Repair of Articular Cartilage. J. Rheumatol., 1:1–10.
40. Sokoloff, L., 1978: In Vitro Culture of Skeletal Tissues, Ch. I, pp. 1–27, Vol. II, in: The Joints and Synovial Fluid. Vols. I & II, L. Sokoloff, Ed., Academic Press, New York, N.Y.
41. Tizzoni, G., 1878: Sulla Isologia Normale e Pathologica delle. Cartilagina Ialine. Arch. per le Sc. Med, 2:27.
42. Zhan, F. W., 1877: Sur La Sort des Tisses Implantes Dans L'ouganisme. Congr. Med. Internat. de Geneve, p. 687.

I claim:
1. A grafting technique for promoting the healing of an articular cartilage lesion comprising the steps of:
   A: producing in vitro autologous cultured chondrocytes prior to grafting;
   B: seeding a collagen matrix with the cultured chondrocytes to provide an activated matrix;
   C: implanting the activated collagen matrix in the lesion to be treated to provide a graft; and

D: mechanically fixing the graft by a periosteal flap sutured to the cartilage so that it remains in place during the healing process.

2. A technique as set forth in claim 1, wherein said matrix is a collagen gel.

3. A technique as set forth in claim 1, wherein said matrix is a collagen sponge.

4. A grafting technique as set forth in claim 1, wherein said collagen matrix is constituted by a collagen gel in which the chondrocytes are dispersed prior to its polymerization.

* * * * *